US005585724A

United States Patent [19]
Morich et al.

[11] Patent Number: 5,585,724
[45] Date of Patent: Dec. 17, 1996

[54] MAGNETIC RESONANCE GRADIENT COILS WITH INTERSTITIAL GAP

[75] Inventors: Michael A. Morich, Mentor; Labros S. Petropoulos, Solon, both of Ohio

[73] Assignee: Picker International, Inc., Highland Heights, Ohio

[21] Appl. No.: 488,166

[22] Filed: Jun. 12, 1995

[51] Int. Cl.$^6$ ............................................. G01V 3/00
[52] U.S. Cl. ............................................. 324/318; 128/653.3
[58] Field of Search ................................ 324/300, 307, 324/309, 310, 311, 312, 313, 314, 318, 322; 128/653.1, 653.2, 653.3

[56] References Cited

U.S. PATENT DOCUMENTS

| | | | |
|---|---|---|---|
| 4,689,591 | 8/1987 | McDougall | 335/299 |
| 4,847,985 | 7/1989 | Aubert | 29/605 |
| 5,012,192 | 4/1991 | Siebold | 324/318 |
| 5,045,792 | 9/1991 | Mehdizadeh | 324/318 |
| 5,278,504 | 1/1994 | Patrick et al. | 324/318 |
| 5,296,810 | 3/1994 | Morich | 324/318 |
| 5,349,297 | 9/1994 | DeMeester et al. | 324/318 |
| 5,378,989 | 1/1995 | Barber et al. | 324/318 |

FOREIGN PATENT DOCUMENTS

WO86/04687  8/1986  WIPO .

*Primary Examiner*—Michael Tokar
*Attorney, Agent, or Firm*—Fay, Sharpe, Beall, Fagan, Minnich & McKee

[57] ABSTRACT

A patient support (40) has lower sections (50a, 50b) of first and second gradient coil assembly portions (42a, 42b) affixed thereto. Upper sections (52a, 52b) of the gradient coil assembly portions are selectively removable from the lower gradient coil assembly sections. The gradient coil assembly sections are mounted such that an interstitial gap is defined therebetween. The gradient coil assembly portions are configured to fit snugly around the patient's torso below the shoulders and around the patient's head, but are too small in diameter to pass around the patient's shoulders. The radio frequency coil (44) has a lower portion (60) disposed below the patient's shoulders and an upper portion (62) removably positionable above the patient's shoulders. The gap between the two gradient coil assembly portions is preferably between ½ and ¾ of a diameter of the gradient coil portions. An invasive medical instrument, such as a biopsy gun (100), is mounted to the patient support adjacent the gap between the gradient coil portions for performing invasive medical procedures on a portion of the patient through the gap between the gradient coil portions.

7 Claims, 5 Drawing Sheets

MAGNETIC RESONANCE GRADIENT COILS WITH INTERSTITIAL GAP

BACKGROUND OF THE INVENTION

The present application relates to the magnetic resonance imaging arts. It finds particular application in conjunction with magnetic resonance imaging of the torso of human subjects and will be described with particular reference thereto. It is to be appreciated, however, that the present invention also finds application in conjunction with imaging other parts of the human anatomy and with the imaging of non-human and inanimate subjects.

In magnetic resonance imaging, dipoles are selectively aligned with a primary magnetic field. Radio frequency excitation pulses are applied to stimulate resonance in the aligned dipoles and radio frequency magnetic resonance signals are collected from the resonating dipoles. Gradient magnetic field pulses are applied to encode spatial position. When imaging the upper torso, which includes the heart and other moving tissue, high speed image acquisition is advantageous.

To promote high speed image acquisition and high resolution, high strength magnetic field gradients with high slew rates are advantageous. That is, gradients of large magnitude that can be switched on and off very quickly improve data acquisition time and resolution. However, gradient strength varies inversely as the radius squared of the gradient coil and stored energy, a critical factor for slew rate, varies with the fifth power of the radius of the gradient coil.

To improve data acquisition speed at resolution in other parts of the human anatomy, smaller diameter gradient coils have been used, e.g., smaller diameter head or wrist coils. However, the width of the patient's shoulders has been a limiting consideration for upper torso imaging.

To improve the magnetic field gradient characteristics in the upper torso, elliptical gradient coils and planar gradient coils have been utilized.

Another drawback of whole body coils, insertable coils, and local coils is that they limit access to the examined patient. The gradient coils substantially surround the examined region. In order for a physician to gain access to the examined region, such as for a biopsy, the patient must be removed from the gradient coil assembly. Moving the patient relative to the gradient coil assembly also moves the patient relative to the resultant image. The moved patient needs to be reregistered with the diagnostic image.

Typically, a head coil is on the order of 30 cm in diameter; whereas, a whole body gradient magnetic field coil is about 65 cm in diameter. Larger diameter gradient coils are typically positioned close to the main magnetic field coils in order to minimize main magnetic field coil diameters. When the gradient and main magnetic field coils are placed closely adjacent, the gradient coil assemblies tend to induce eddy currents in the main magnetic field coil assembly. Shield gradient coils are typically disposed between the gradient and main magnetic field coils to inhibit eddy currents. However, the shield gradient coils increase gradient coil power consumption, typically by about a factor of 2.

The present invention provides a new and improved gradient magnetic coil assembly for magnetic resonance imaging which overcomes the above-referenced problems and others.

SUMMARY OF THE INVENTION

In accordance with the present invention, a magnetic resonance imaging apparatus is provided. A primary magnet assembly generates a temporally constant magnetic field through an examination region. A gradient coil assembly induces magnetic field gradients across the examination region. A radio frequency coil receives resonance signals from the examination region. The gradient coil includes first and second gradient coil portions which are physically separated by an interstitial gap. The first and second gradient coil portions which are disposed on opposite sides of the examination region have internal windings for generating gradient magnetic field components along three mutually orthogonal axes.

In accordance with a more limited aspect of the present invention, the gradient coil assemblies are circularly cylindrical and the interstitial gap is at least ½ a diameter of the cylindrical gradient coil portions.

In accordance with another more limited aspect of the present invention, at least one of the gradient coil portions has upper and lower sections which are selectively separable.

In accordance with another more limited aspect of the present invention, one of the gradient coil portions extends around the patient's torso below the shoulders and the other extends around the patient's head and neck above the shoulders. In this manner, an upper torso region of the patient can be imaged with a gradient coil assembly that is smaller in diameter than the width of the patient's shoulders.

In accordance with another aspect of the present invention, an invasive medical instrument is mounted in a selected relationship to the subject for insertion through the interstitial gap.

In accordance with another aspect of the present invention, a magnetic resonance imaging system is provided. A toroidal dewar contains a superconducting magnet for generating a temporally constant magnetic field axially through a longitudinal bore of the dewar. A patient support is selectively insertable into the bore. A gradient coil assembly includes a first gradient coil portion fixedly mounted to the patient support and a second gradient coil portion mounted in a fixed relationship to the first gradient coil portion, when the patient is inserted into the bore. When the first and second gradient portions are in said fixed relationship, there is an interstitial gap between the two gradient coil assembly portions. A radio frequency coil is mounted adjacent a region of a subject supported by the patient support in the interstitial gap between the first and second gradient coil assembly portions. A radio frequency transmitter is connected with the radio frequency coil for selectively transmitting radio frequency magnetic resonance excitation and manipulation signals to the radio frequency coil. A radio frequency receiver is connected with the radio frequency coil for receiving magnetic resonance signals from the region of the subject in the interstitial gap. An image reconstruction processor reconstructs the received magnetic resonance signals into an image representation. An image memory stores the electronic image representation. A video processor selectively converts portions of the stored image representation into an appropriate format for display on a human-readable monitor.

In accordance with another more limited aspect of the present invention, a vacuum dewar has a window therethrough to provide human access to a central portion of the longitudinal bore.

In accordance with another aspect of the present invention, a method of magnetic resonance imaging is provided. The imaging is performed with a magnetic resonance imaging system that includes a toroidal dewar that contains a superconducting magnet assembly which defines an axial bore therein. A patient support is selectively insertable into and removable from the axial bore. A gradient coil assembly has a first gradient coil assembly portion and a second gradient coil assembly portion which are separated by an interstitial gap. The first and second gradient coil assembly portions each have lower sections which are fixedly mounted to the patient support and upper sections which are selectively removable therefrom. A radio frequency assembly has a first gradient coil portion which is fixedly supported by the patient support between the first and second gradient coil assembly portions and an upper portion which is selectively positionable above an upper torso portion of the subject between the first and second gradient coil assembly portions. The gradient coil assembly upper sections are removed. A patient is positioned on the support with the patient's torso below the shoulders in one of the gradient coil assembly lower sections and the patient's head and neck in the other gradient coil assembly lower section. The first-and second gradient coil assembly upper sections are connected to the lower sections. The radio frequency coil assembly upper portion is disposed over the patient's upper torso portion. At least the upper torso portion of the patient and the first and second gradient coil assembly portions are positioned in the bore. A magnetic resonance imaging sequence is conducted to generate an image representation of at least the upper torso portion of the patient. A portion of the electronic image representation is selectively displayed as a human readable display.

One advantage of the present invention is that it improves the resolution of torso images.

Another advantage of the present invention resides in the improved imaging speeds and data acquisition times in torso imaging.

Another advantage of the present invention is that it facilitates access to the examined region of the patient, while the patient is still disposed in a known relationship to the gradient magnetic field coils.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
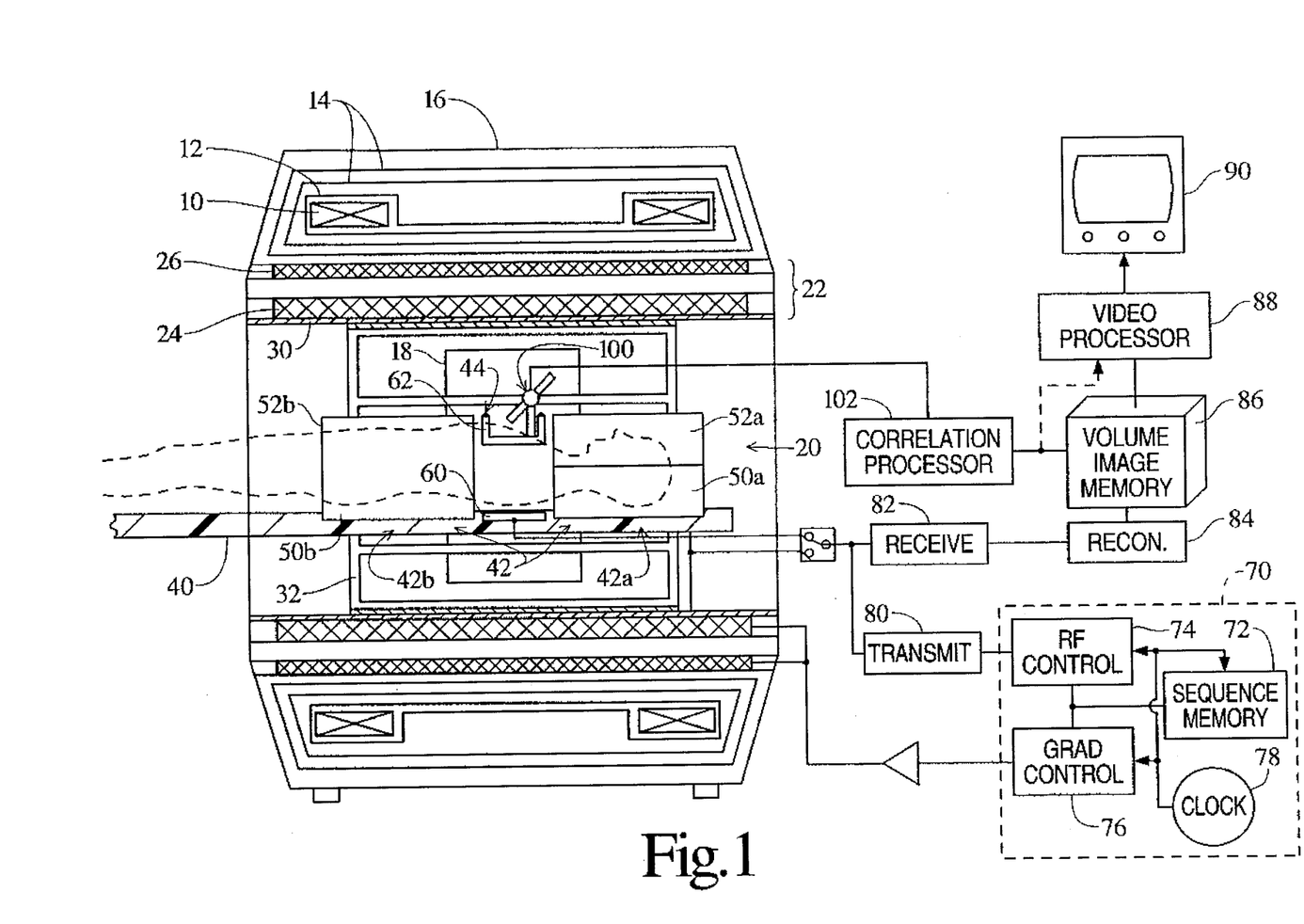
FIG. 1 is a diagrammatic illustration of a magnetic resonance imaging system in accordance with the present invention.

With reference to FIG. 1, a magnetic resonance imaging system includes main or primary magnets 10. In the preferred embodiment, the main or primary magnets are annular superconducting magnets disposed adjacent opposite ends of the assembly within a liquid helium can 12. The liquid helium can and the magnets are surrounded by a plurality of cold shields 14 which assist in maintaining the superconducting magnets at superconducting temperatures while minimizing helium boil off. The magnet assembly is surrounded by a toroidal vacuum dewar 16. Between the magnets adjacent opposite sides of the center of the bore, windows 18 are cut through the vacuum dewar, cold shields, helium can to provide access to the patient. The helium can, cold shields, and the vacuum dewar are, of course, closed around the windows to maintain their integrity.

The vacuum dewar and the magnet assembly define a central bore 20. A gradient coil assembly, preferably a self-shielded whole body gradient coil assembly 22 is disposed around an outer periphery of the bore 20. In the illustrated embodiment, the whole body gradient coil assembly 22 includes a primary gradient coil assembly 24 within the bore which includes x, y, and z-whole body gradient coil windings for generating magnetic field gradients along x, y, and z-directions. A shield gradient coil assembly 26 is disposed inside the vacuum dewar for cancelling the magnetic field gradients emanating toward the main magnet assembly. A radio frequency shield 30 lines an inner surface of the gradient coil assembly. The radio frequency shield is transparent to gradient (kHz) range magnetic fields but is opaque to radio frequency (MHz) signals. A whole body radio frequency coil 32, such as a birdcage style coil, is disposed around the inner surface of the radio frequency shield 30 surrounding the bore 20.

A retractable patient support 40 supports a subject to be examined, an insertable gradient coil assembly 42, and an insertable radio frequency coil assembly 44. The gradient coil assembly 42 includes a first or head gradient coil portion 42a and a second or lower abdominal cavity gradient coil portion 42b.

Figure 2:
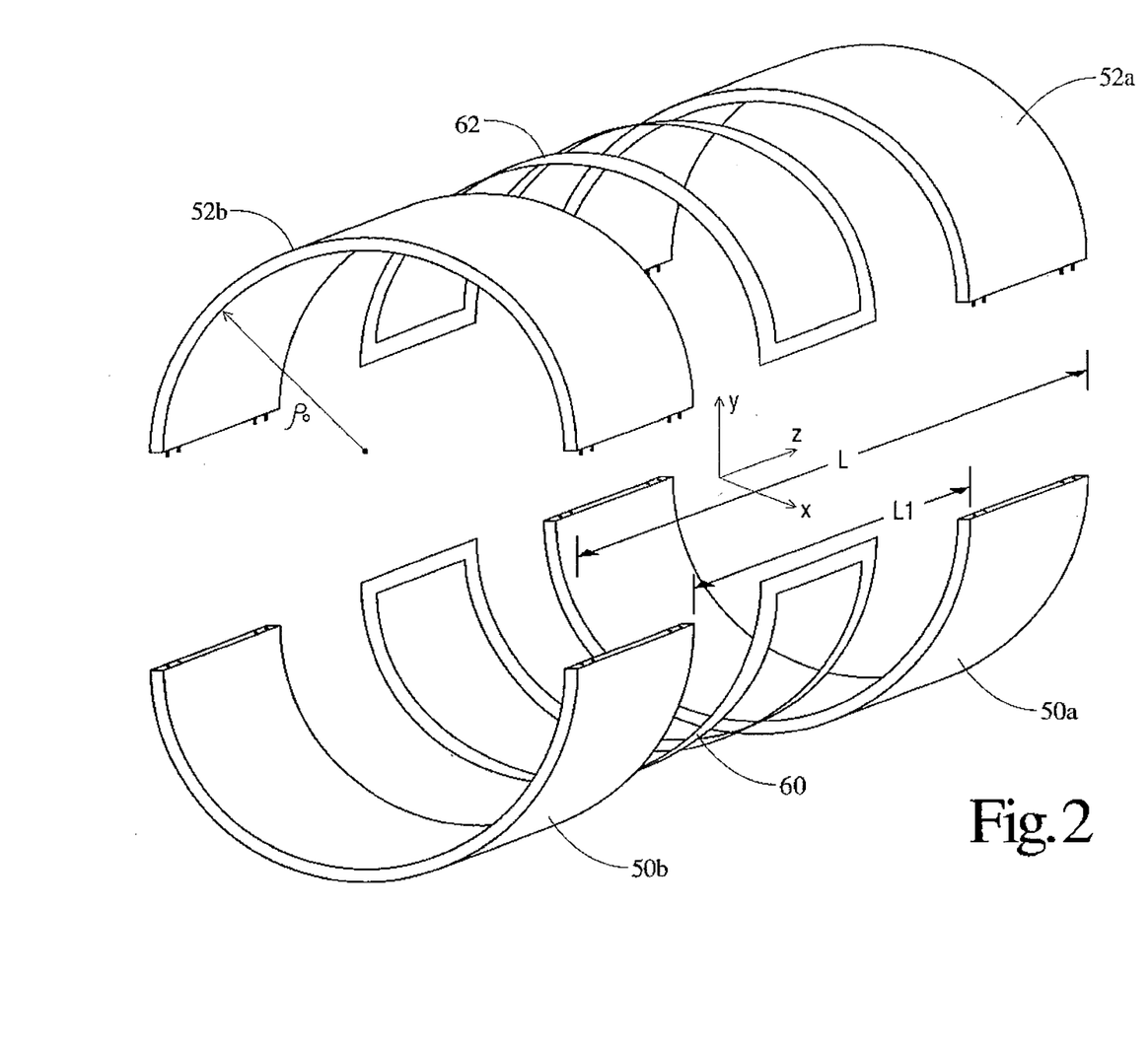
FIG. 2 is an expanded view of the gradient and radio frequency coil assembly of FIG. 1.
Figure 3:
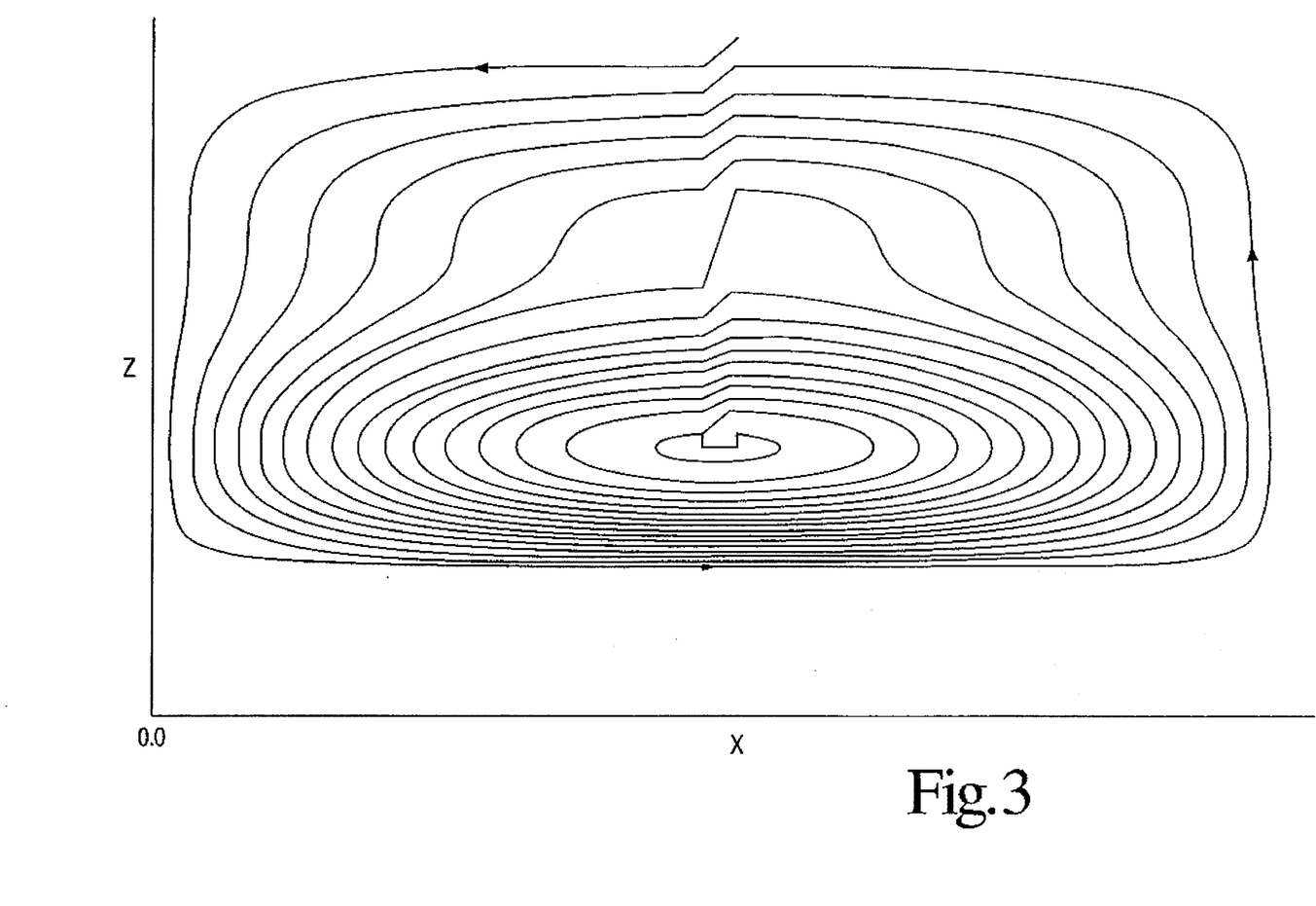
FIG. 3 is a detailed view of one quadrant of an x or y-gradient coil distributed gradient coil winding.

With continuing reference to FIG. 1 and further reference to FIG. 2, the first gradient coil portion 42a includes a lower portion 50a which is mounted to the patient support 40. An upper, selectively removable portion 52a is electrically and mechanically interconnected with the lower portion 50a for imaging and is released and removed to facilitate patient access. In the preferred embodiment, the upper and lower gradient coil assemblies are constructed on a rigid dielectric former. The upper and lower assemblies together carry a pair of x-gradient coil assemblies as illustrated in FIG. 3 and a pair of y-gradient coil assemblies also as illustrated in FIG. 3. The x and y-gradient coils are disposed 90° offset around a central axis of the bore 20. Z-gradient coils in the form of annular loops are also carried by the dielectric formers. In the preferred embodiment, the x and y-gradient coils are constructed of copper foil laminated to the dielectric former. Electrical connectors, such as metal pins and sockets are mounted in the upper and lower former portions for providing electrical continuity between coil portions on the upper and lower coil portions when the coil portions are assembled together.

The second gradient coil portion 42b also has a lower portion 50b mounted to the patient support 40 and an upper removable portion 52b. The upper and lower portions again are constructed of a rigid dielectric material to which x and y-gradient coils, preferably of the construction of FIG. 3 are laminated along with annular z-gradient coils. Electrical pins or other connectors again provide electrical connection between coil portions on the upper and lower portions when assembled.

The radio frequency coil 44 in the illustrated embodiment, includes a lower saddle coil 60 mounted to the patient support closely adjacent and generally conforming to the patient's back. An upper saddle coil 62 is removably mounted closely adjacent to the patient's chest. The upper radio frequency coil preferably has an arc which generally conforms to the curvature of the patient's upper torso across the shoulders. Alternately, as illustrated in FIG. 2, the radio frequency coil may be a circular coil with a diameter larger than the patient's shoulders, or an elliptical coil with its major diameter selected to receive a patient's shoulders and minor diameter dimensioned to receive the patient's chest.

In the preferred embodiment, the two gradient coil portions 42a, 42b each have a common diameter of 40–45 cm, with 42 cm being preferred. The coil portions 42a and 42b are separated from each other by up to 30 cm, with 20–30 cm of separation being preferred. In this manner, the separation between the gradient coil portions is preferably between ½ and ¾ of the gradient coil diameter.

In operation, a sequence control 70 generates the appropriate gradient and radio frequency pulses of a selected magnetic resonance imaging sequence. More specifically, the characteristics of a selected magnetic resonance imaging sequence are withdrawn from a sequence memory 72 and stored and used to control a radio frequency sequence controller 74 and a gradient pulse controller 76. A common clock 78 clocks the radio frequency and gradient controllers simultaneously. The selected radio frequency pulse signals are conveyed to a radio frequency transmitter 80 which is selectively connectable to the whole body radio frequency coil 32 and the insertable radio frequency coil 44.

After magnetic resonance is induced, the insertable radio frequency coil 44 or a surface coil (not shown) receives the magnetic resonance signal and conveys it to a digital receiver 82. The digital receiver 82 demodulates and digitizes the magnetic resonance signal. A reconstruction processor 84 reconstructs the received magnetic resonance signals into a volumetric or slice image representation. A volume image memory 86 stores one or a series of image representations from the reconstruction processor. A video processor 88 converts selected portions of the image representations in the image memory 86 into appropriate format for display on a monitor 90. For example, the video processor may convert selected slices of an imaged volume into appropriate format for display. As another option, the video processor can select the corresponding slice in a series Of temporally displaced images of the heart to provide a cine image representation which simulates a motion picture of the selected slice of the heart as the heart is beating. As yet another example, the video processor can assembly a three-dimensional rendering of a selected organ or region.

Based on the image representation, various diagnostic and medical procedure options are available. In the preferred embodiment, a non-ferrous medical instrument, such as a biopsy gun 100 is mounted to the patient support 40. The biopsy gun is adjustably positionable relative to the patient, e.g., its height, angle, or axial position. In the preferred embodiment, the radio frequency coil 44 is a saddle coil which is defined by conductors having large open regions therebetween. The medical instrument is positioned to pass through the open regions of the radio frequency coil. In one embodiment, electromechanical sensors sense the position adjustments of the biopsy gun to provide an electrical indication of the selected biopsy needle trajectory relative to a fixed coordinate system of the patient support 40. Magnetic resonance detectable elements, such as spheres of copper sulfate, are embedded in the patient support 40 under the central portion. These magnetic resonance markers produce characteristic, corresponding elements in the reconstructed volume image representations stored in the image memory 86. The magnetic resonance markers provide a fixed correlation between the reconstructed image representations and the preselected fixed frame of reference of the patient support 40. A frame of reference correlation processor 102 correlates the frame of reference of the image representations with the location of the biopsy gun 100 or other medical instrument. More specifically to the preferred embodiment, the correlation processor generates an indication of the trajectory of the biopsy gun relative to the frame of reference of the reconstructed video image and conveys such trajectory information to the image memory 86 and the video processor 88. The video processor superimposes the trajectory on the displayed image representation to provide a direct indication to the physician of the selected trajectory relative to the internal regions of the patient.

Various other techniques for correlating the position of the biopsy gun or other medical instrument with the frame of reference of the patient and the patient support 40 are also contemplated. For example, the medical instrument may carry sonic, optical, radio frequency, or other emitters which selectively emit signals that are received by corresponding receivers mounted to the patient support 40 in a known relationship. By triangulating the signals received by the receivers based on time of flight, angle of reception, and the like, the exact position of each emitter relative to the receivers, hence the coordinate system of the patient support 40, is readily calculable.

The window 18 enables the physician to position the biopsy gun or other medical instrument manually while monitoring its trajectory on the monitor 90. Alternately, the instrument may be positioned remotely using servomotors or the like. Once the desired trajectory is attained, other images through the trajectory are displayed to be sure that the trajectory does not pass through an inappropriate organ or tissue. Thereafter, the physician inserts a biopsy needle, for example, along the trajectory for a distance measured from the display on the monitor 90 to perform the biopsy. Analogously, other medical instruments may be inserted along the trajectory to perform other medical procedures. As yet another alternative, the biopsy gun may be spring loaded or mechanically driven. Other electrically controlled medical instruments may also be used.

In the preferred embodiment, the gradient coils generate a gradient magnetic field on the order of 80–100 mT/m with rise times on the order of 250 μsec. The generated magnetic field gradient should be linear in the region of interest centered between the coils, anti-symmetric around the origin along the z or longitudinal axis, and symmetric around the origin along x and y-axes orthogonal to the z-axis and each other. For a maximum gradient coil length of L and an interstitial gap of $L_1$, these gradient characteristics are achieved from a current distribution that is limited to the regions from $-L/2$ to $-L_1/2$ and from $L_1/2$ to $L/2$.

Looking first to the design of the z-gradient coil, the resultant magnetic field gradient varies linearly along the z-direction and is anti-symmetric around the origin at the geometric center of the cylinder. The z-component of the magnetic field is also homogeneous in the plane which is perpendicular to the z-axis, i.e., in the transverse direction. Because there is a linear relation between the current and the magnetic field, the current density of the coil satisfies similar symmetry conditions with the magnetic field. Further, because the gradient coil has a finite physical size, the current density is zero outside of the cylinder. The expression of the Fourier expansion around the geometric center for current for the gradient coil in this design is:

$$j_\phi^a(z) = \begin{cases} 0 \text{ for } |z| \leq \frac{L_1}{2} \\ \sum_{n=1}^{\infty} j_n^a \sin k_{Ln} z \cos k_{1n} z \text{ for } \frac{L_1}{2} \leq |z| \leq \frac{L}{2} \\ 0 \text{ for } |z| \geq \frac{L}{2} \end{cases} \quad (1)$$

where $j_n^a$ are the Fourier coefficients in the expression and the $\sin k_{Ln} z \cos k_{1n} z$ represents the anti-symmetry condition of the current around the origin. Prohibiting current in the gap $L_1$ and outside the physical boundaries of the coil limits the values that $k_{Ln}$ and $k_{1n}$ can assume. Thus, the set of allowable values for $k_{Ln}$ and $k_{1n}$ are:

$$j_\phi^a\left(\pm \frac{L_1}{2}\right) = 0 \text{ then } k_{1n} = \frac{(2n-1)\pi}{L_1}, \quad (2)$$

$$j_\phi^a\left(\pm \frac{L_1}{2}\right) = 0 \text{ then } k_{Ln} = \frac{2n\pi}{L}. \quad (3)$$

It is to be recognized by those of ordinary skill in the art that other end conditions can also be used, e.g., the current is not required to go to zero.

Because the expression of the magnetic field contains the Fourier transform of the current density, the Fourier transform of the current density which has the form of Equation (1) is calculated. The Fourier transform pairs for $j_\phi^a$ are defined as follows:

$$j_\phi^a(k) = \int_{-\infty}^{+\infty} j_\phi^a(z) e^{-ikz} dz, \quad (4a)$$

$$j_\phi^a(z) = \frac{1}{2\pi} \int_{-\infty}^{+\infty} j_\phi^a(k) e^{+ikz} dk. \quad (4b)$$

Considering the above-expressions, the Fourier transform of $j_\phi^a(z)$ is:

$$j_\phi^a(k) = \sum_{n=1}^{\infty} i \frac{L}{4} j_n^a \psi_n(k), \quad (4c)$$

with:

$$\psi_n(k) = \quad (5)$$

$$\left[ -\frac{\sin(k - k_{Ln} - k_{1n}) \frac{L}{2}}{(k - k_{Ln} - k_{1n}) \frac{L}{2}} + \frac{\sin(k + k_{Ln} - k_{1n}) \frac{L}{2}}{(k + k_{Ln} - k_{1n}) \frac{L}{2}} - \right.$$

$$\frac{\sin(k - k_{Ln} + k_{1n}) \frac{L}{2}}{(k - k_{Ln} + k_{1n}) \frac{L}{2}} + \frac{\sin(k + k_{Ln} + k_{1n}) \frac{L}{2}}{(k + k_{Ln} + k_{1n}) \frac{L}{2}}$$

$$-\frac{L_1}{L} \left[ \frac{\sin(k - k_{Ln} - k_{1n}) \frac{L_1}{2}}{(k - k_{Ln} - k_{1n}) \frac{L_1}{2}} - \frac{\sin(k + k_{Ln} - k_{1n}) \frac{L_1}{2}}{(k + k_{Ln} - k_{1n}) \frac{L_1}{2}} + \right.$$

$$\left. \frac{\sin(k - k_{Ln} + k_{1n}) \frac{L_1}{2}}{k - k_{Ln} + k_{1n}) \frac{L_1}{2}} - \frac{\sin(k + k_{Ln} + k_{1n}) \frac{L_1}{2}}{(k + k_{Ln} + k_{1n}) \frac{L_1}{2}} \right]$$

It should be noted that the dependence of $\psi_n(k)$ on the sign of k is:

$$\psi_n(-k) = -\psi_n(k) \quad (6).$$

From the expression for the Fourier component of the current, the expression of the magnetic field in terms of the Fourier coefficients is:

$$B_z = \frac{\mu_0 a}{2\pi} \int_{-\infty}^{+\infty} dk e^{ikz} k \sum_{n=1}^{\infty} i \frac{L}{4} j_n^a \psi_n(k) I_0(k\rho) K_1(ka). \quad (7)$$

Because $\psi_n(k)$ is an odd function of k, the integral of Equation (7) is zero, unless the complex exponential is only an odd function of k. Accordingly, replacing $e^{ikz}$ by $i\sin(kz)$, Equation (7) for the magnetic field can be expressed as:

$$B_z = -\frac{\mu_0 a}{2\pi} \int_{-\infty}^{+\infty} dk \sin kz k \sum_{n=1}^{\infty} \frac{L}{4} j_n^a \psi_n(k) I_0(k\rho) K_1(ka). \quad (8)$$

Using the relationship:

$$|j_\phi^a(k)|^2 = \sum_{n=1}^{\infty} \sum_{n'=1}^{\infty} j_n^a j_{n'}^a \frac{L^2}{16} \psi_n(k) \psi_{n'}(k), \quad (9)$$

the stored magnetic energy $W_m$ is:

$$W_m = \frac{a^2 \mu_0}{2} \int_{-\infty}^{\infty} dk I_1(ka) K_1(ka) \sum_{n=1}^{\infty} \sum_{n'=1}^{\infty} j_n^a j_{n'}^a \frac{L^2}{16} \psi_n(k) \psi_{n'}(k). \quad (10)$$

From expressions of the magnetic field and the stored energy, the functional $\mathscr{E}$ is defined as:

$$\mathscr{E}(j_n^a) = W_m - \sum_{j=1}^{N} \lambda_j (B_z(\vec{r}_j) - B_{zSC}(\vec{r}_j)). \quad (11)$$

Minimizing $\mathscr{E}$ with respect to $j_n^a$, a matrix equation for $j_n^a$ is defined as:

$$\sum_{n'=1}^{\infty} j_{n'}^a \left\{ \frac{aL\pi}{2} \int_{-\infty}^{\infty} dk I_1(ka) K_1(ka) \psi_n(k) \psi_{n'}(k) \right\} = \quad (12a)$$

$$-\sum_{j=1}^{N} \lambda_j \int_{-\infty}^{\infty} dk k \sin kz_j I_0(k\rho_j) K_1(ka) \psi_n(k),$$

or:

$$\sum_{n'=1}^{\infty} j_{n'}^a C_{n'n} = \sum_{j=1}^{N} \lambda_j D_{jn}. \quad (12b)$$

Truncating the infinite summations at M terms, the matrix representation of Equation (12b) becomes:

$$\underline{J}^a \underline{C} = \underline{\lambda} \underline{D} \quad (13a),$$

or:

$$\underline{J}^a = \underline{\lambda} \underline{D} \underline{C}^{-1} \quad (13b),$$

where $\underline{J}^a$ is a 1×M matrix or vector, $\underline{C}$ is an M×M matrix, $\underline{\lambda}$ is a 1×N matrix or vector, and $\underline{D}$ is a N×M matrix. The Lagrange multipliers can be found using the expression of the magnetic field. Then the matrix representation of the magnetic field is:

$$B_z(r_j) = \sum_{n=1}^{M} j_n^a D_{jn}, \quad (14a)$$

or:

$$\underline{B}_z = \underline{J}^a \underline{D}^t, \quad (14b)$$

where $\underline{B}_z$ is a 1×N matrix or vector, and the superscript t is the symbol for the transpose of the matrix. By replacing $\underline{J}^a$ from Equation (13b) in Equation (14b), the expression of the magnetic field becomes:

$$\underline{B}_z = \underline{\lambda} \underline{D} \underline{C}^a \underline{D}^t \quad (b\ 15),$$

which leads to the determination of Lagrange multipliers as:

$$\underline{\lambda} = \underline{B}_z [\underline{DC}^{-1}\underline{D}^t]^{-1} \quad (16),$$

providing that the inverse matrix of the expression $[\underline{DC}^{-1}\underline{D}^t]$ exists. Upon determination of the Lagrange multipliers, the expression for the Fourier components of the current density in matrix form becomes:

$$\underline{J}^a = \underline{B}_z [\underline{DC}^{-1}\underline{DC}]^{-1} \quad (17).$$

In this manner, the expression for the Fourier components for the gradient coil is determined. Substituting back into the expression for current density, the continuous current distributions of the current density for the coil are readily determined.

The continuous current density is divided by a discretization process with axially varying current densities to determine discrete current winding patterns for the coil. The continuous current distribution is divided into positive and negative current regions. Integrating the area underneath each region generates the total current which is contained in each region. Once the current for all regions of the cylinder is calculated, discrete current loops are placed in order to mimic the behavior of the continuous current pattern. Each of the regions is then filled with discrete wires carrying a prescribed amount of current which is the same for all wires. The most probable value of the current is found and the behavior of the discrete current values is related closer to a continuous current density. More specifically, each region of the continuous current density is divided into smaller segments which correspond to equal amounts of current. Then, each wire or foil strip is placed through the middle of the segment in order to obtain an equal contribution from both sides of the segment. Alternately, one can calculate these values based on the center of mass technique described in U.S. Pat. No. 5,296,810 of Morich.

Optionally, a shield gradient coil is provided to eliminate eddy current effects. In order to eliminate magnetic field gradients outside of the region of interest, while maintaining the above-described magnetic field conditions inside the region of interest, the relationship between the current density of the outer coil $j_z^a(k)$ and the inner coil $j_z^a(k)$ in the Fourier domain is:

$$j_\phi^b(k) = -\frac{aI_1(ka)}{bI_1(kb)} j_\phi^a(k). \quad (18)$$

In this example, the kernals in the integral expressions for the total magnetic field and the stored magnetic energy are modified by multiplying with a factor $S_{ab}$ defined as:

$$S_{ab} = \begin{cases} 1 \text{ for non-shielded design} \\ \left(1 - \frac{I_1(ka)K_1(kb)}{I_1(kb)K_1(ka)}\right) \text{ for shelf-shielded design.} \end{cases} \quad (19)$$

In the preferred embodiment, the gradient coil has a radius of 21 cm, a total length of 90 cm, and an interstitial gap of 30 cm. The Fourier series expansion was limited to 10 terms (M=10). Three constraint points were chosen to define the characteristics of the field inside a 25 cm spherical volume. The first constraint establishes a gradient field with a strength of 40 mT/m. The second constraint defines a linearity at a distance of 12.5 cm from the center of coil as varying not more than 5% of the ideal value, in the preferred embodiment. The third constraint defines the uniformity across the plane perpendicular to the gradient axis to be less than 15%, in the preferred embodiment. These constraints are displayed in TABLE 1.

TABLE 1

| n | $\rho_i$ | $z_i$ | $B_{zSC}(2n)$ |
|---|---|---|---|
| 1 | 0.0000 | 0.001 | 0.00004000 |
| 2 | 0.0000 | 0.125 | 0.00500000 |
| 3 | 0.1250 | 0.001 | 0.00003440 |

Figure 4:
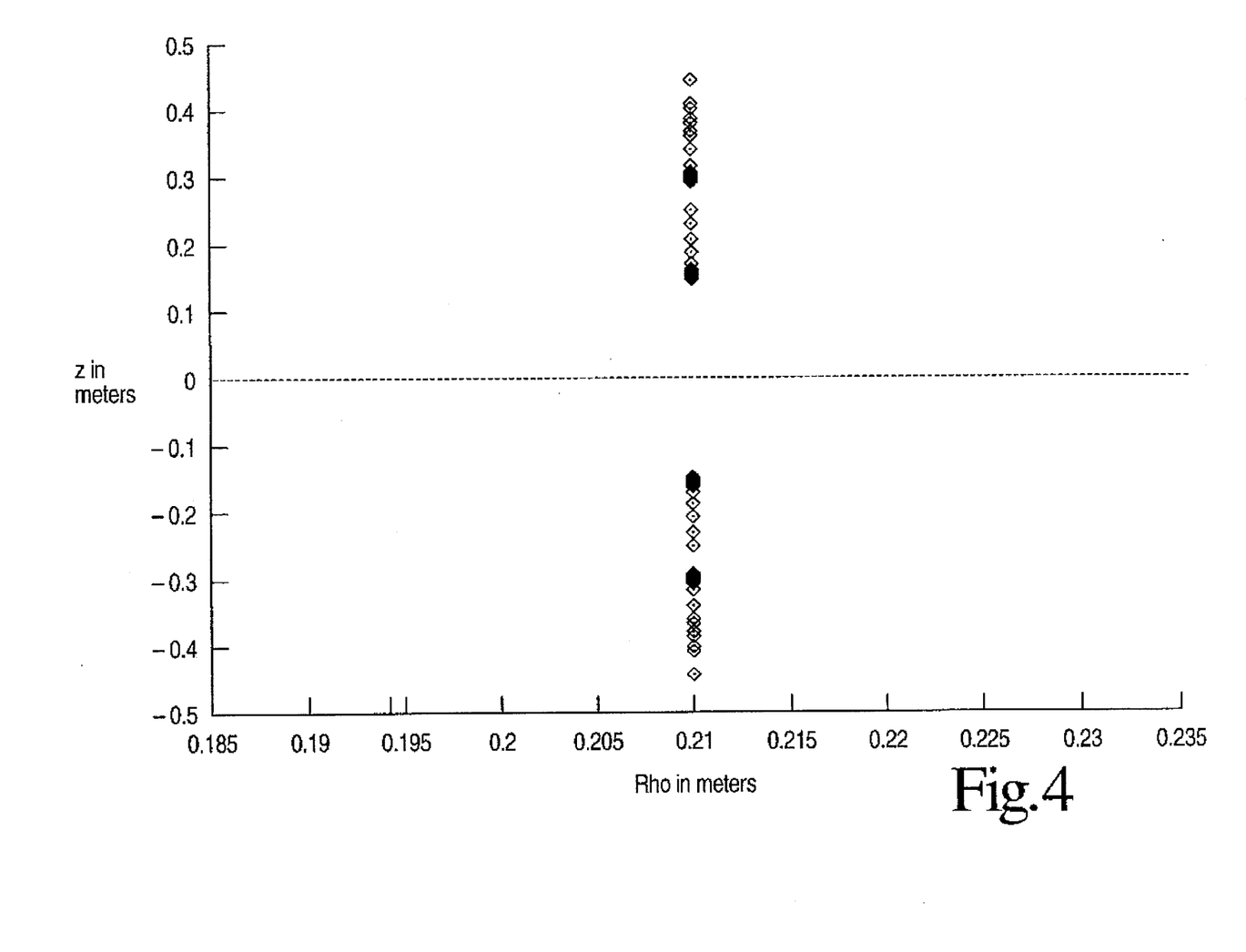
FIG. 4 illustrates a preferred distributed z-gradient coil winding pattern.

Discretizing the current, a series of 18 negative and positive regions are defined as illustrated in FIG. 4, which illustrates the axial spacing of winding loops which each carry a common current. The winding pattern illustrated in FIG. 4 achieves a magnetic field gradient of 38.83 mT/m at 170 amps, a linearity along the gradient axis of 0.7% at $z = \pm 12.5$ cm, and a uniformity of the gradient field inside the spherical volume of 13.57%. The calculated stored energy is 33.63 Joules at 100.5 mT/m gradient strength which achieves a rise time of $t_r$ of 264.5 μsec. for a current of 440 Amps and a voltage of 600 volts. The corresponding slew rate is SR=380 mT/m/msec. TABLE 2 illustrates a comparison of a conventional whole self-shielded body gradient coil (diameter=68 cm) and the above-described coil:

TABLE 2

| Property | CONVENTIONAL | INTERSTITIAL |
|---|---|---|
| Strength @ 440 Amps | 28 mT/m | 100.5 mT/m |
| SLEW RATE @ 600 Volts | 75 mT/m/msec | 380 mT/m/msec |
| Linearity @ z = ±12.5 cm | 0.7% | 0.7% |
| Uniformity @ ρ = ±12.5 cm | 1.5% | 13.6% |

The transverse gradient coils again are designed by limiting the current to lie on the surface of the cylinder. The total current density for this current design can be represented as a superposition of two components, one along the axial and the other along the azimuthal direction. The current density is again limited to the region between the ends of the coil and the ends of the interstitial gap. For a transverse gradient coil, the total current density can be described as:

$$\vec{j}^a(\vec{r}) = [j_{100}^a(\phi,z)\hat{a}_{100} = j_z^a(\phi,z)\,\hat{a}_z]\delta(\rho-\rho_o) \quad (20),$$

where $\delta(\rho-\rho_o)$ is the restriction that the current is defined on the cylindrical surface of radius $\rho_o = a$. The restriction on the total length of the coil, the confinement of the current density to the cylindrical surface, the azimuthal and axial symmetries for $j_{100}^a$ and $j_z^a$ and the requirement that the current density obeys the continuity equation provides a Fourier series expansion for both components around the geometric center of the coil as:

$$j_\phi^a(\phi,z) = \begin{cases} 0 \text{ for } |z| \leq \frac{L_1}{2} \\ \cos\phi \sum_{n=1}^{\infty} j_{\phi n}^a \cos k_n z \text{ for } \frac{L_1}{2} \leq |z| \leq \frac{L}{2}, \\ 0 \text{ for } |z| \geq \frac{L}{2} \end{cases} \quad (21)$$

$$j_z^a(\phi,z) = \begin{cases} 0 \text{ for } |z| \leq \frac{L_1}{2} \\ \sin\phi \sum_{n=1}^{\infty} \frac{j_{\phi n}^a}{k_n a} \sin k_n z \text{ for } \frac{L_1}{2} \leq |z| \leq \frac{L}{2}, \\ 0 \text{ for } |z| \geq \frac{L}{2} \end{cases} \quad (22)$$

where $j_{\phi n}^a$ are Fourier coefficients, L is the total length of the inner coil, and $k_n = 2n\pi/L$, because the current cannot flow off the ends of the cylinder. The general expression of the magnetic field for a transverse gradient coil in terms of the Fourier transform of the current density is:

$$B_z = \qquad (23)$$

$$-\frac{\mu_0 a}{2\pi} \sum_{m=-\infty}^{\infty} e^{+im\phi} \int_{\infty}^{-\infty} dk k e^{+ikz} j_\phi{}^a(m,k) I_m(k\rho) K_m'(ka),$$

where $j_\phi{}^a(m,k)$ is the double Fourier transform of $j_{100}{}^a(\phi,z)$. Since the azimuthal dependence of $j_{100}{}^a$ is proportional to $\cos\phi$, the Fourier transform of $j_{100}{}^a$ is non-zero when $m=\pm 1$. In this case, the two-dimensional Fourier transform of the current density is:

$$j\phi^a(\pm 1,k) = \frac{1}{2}\sum_{n=1}^{\infty} \frac{L}{2} j^a_{\phi n} \psi_n(k), \qquad (24)$$

with:

$$\psi_n(k) = \left[ \frac{\sin(k-k_n)\frac{L}{2}}{(k-k_n)\frac{L}{2}} - \frac{\sin(k-k_n)\frac{L_1}{2}}{(k-k_n)\frac{L}{2}} + \frac{\sin(k+k_n)\frac{L}{2}}{(k+k_n)\frac{L}{2}} - \frac{\sin(k+k_n)\frac{L_1}{2}}{(k+k_n)\frac{L}{2}} \right], \qquad (25)$$

where $\psi_n(k)$ is an even function of $k$ and $j_\phi{}^a(+1,k)=j_{100}{}^a(-1,k)$. Thus, the expression of the gradient field has the form:

$$B_z = -\frac{\mu_0 aL}{4\pi}\cos\phi \sum_{n=1}^{\infty} j^a_{\phi n} \int_{-\infty}^{\infty} k dk \cos kz \psi_n(k) k I_1(k\rho) K_1'(ka) \qquad (26)$$

In a similar fashion, the stored magnetic energy is:

$$W = \qquad (27)$$

$$-\frac{a^2\mu_0 L^2}{16}\sum_{n=1}^{\infty}\sum_{n'=1}^{\infty} j^a_{\phi n} j^a_{\phi n'} \int_{-\infty}^{\infty} dk \psi_n(k)\psi_{n'}(k) I_1'(ka) K_1'(ka).$$

The restriction that the current density be confined to the interval of $L_1/2 \leq |z| \leq L/2$, the assumption that the function which represents the current density distribution is an analytical function of $\phi$ and $z$, and the condition that the current density inside the interstitial gap is zero defines the condition for the z-component of the current density $j_z{}^a(\phi,z)$ at the location $\pm L_1/2$ as:

$$j_z^a\left(\phi, \pm\frac{L_1}{2}\right) = 0 \rightarrow \pm \sum_{n=1}^{\infty} \frac{j^a_{\phi n}}{k_n a} \sin k_n \frac{L_1}{2} = 0. \qquad (28)$$

From the expressions of the magnetic field, the stored energy and the condition for the current density, the functional $\mathscr{E}$ is constructed as:

$$\mathscr{E}(j_n{}^a) = W - \sum_{j=1}^{N_1} \lambda_j(B_z(\vec{r_j}) - B_{zSC}(\vec{r_j})) - \qquad (29)$$

$$\sum_{j=N_1+1}^{N_1+1} \lambda_j \left( j_z^a\left(\pm\frac{L_1}{2}\right) - j^a_{zSC} \right),$$

where $B_{zSC}$ and $j_{zSC}{}^a$ are the prespecified (constraint) values of the magnetic field at the constraint points and for the current density, respectively.

Minimizing $\mathscr{E}$ with respect to $j_{\phi n}{}^a$, a matrix equation for $j_{\phi n}{}^a$ is obtained as:

$$\sum_{n'=1}^{\infty} j^a_{\phi n'}\left\{ \frac{aL\pi}{2}\int_0^{\infty} dk I_1'(ka) K_1'(ka)\psi_n(k)\psi_{n'}(k) \right\} = \qquad (30)$$

$$\sum_{j=1}^{N_1} \lambda_j \cos(\phi_j) \int_0^{\infty} dk k \cos kz_j I_1(k\rho_j) K_1'(ka)\psi_n(k) +$$

$$\sum_{j=N_1+1}^{N_1+1} \lambda_j \frac{4\pi}{\mu_0 L a^2 k_n} \sin k_n \frac{L_1}{2}.$$

Truncating the infinite summation at M terms and using compact notation, Equation (30) reduces to:

$$\sum_{n'=1}^{M} j^a_{\phi n'} C_{n'n} = \sum_{j=1}^{N_1+1} \lambda_j D_{jn}, \qquad (31)$$

or:

$$\underline{J}^a \underline{C} = \underline{\lambda}\underline{D} \text{ or } \underline{J}^A = \underline{\lambda}\underline{D}\underline{C}^{-1}, \qquad (32)$$

where $\underline{J}^a$ is a 1×M matrix or vector, $\underline{C}$ is a M×M matrix, $\lambda$ is a 1×$N_1$+1 vector or matrix, and D is an $N_1$+1×M matrix with:

$$D_{jn} = \begin{cases} B - \text{field for } j = 1, N_1 \\ j^a_{zSC}\left(\pm\frac{L_1}{2}\right) \text{ for } j = N_1+1, N_1+1. \end{cases} \qquad (33)$$

From Equation (32), the Fourier coefficients of the current density expansion can be determined to provide a continuous current distribution for the coil.

Optionally, to eliminate eddy currents, a second or shield gradient coil is provided to shield the region which is outside of both coils. In order for this condition to hold, the relationship between the current density of the outer coil $j_\phi{}^b(k)$ and the inner coil $j_\phi{}^a(k)$ in the Fourier domain is:

$$j_\phi^b(k) = -\frac{aI_1'(ka)}{bI_1'(kb)} j_\phi^a(k). \qquad (34)$$

The expressions for the total magnetic field and the stored magnetic energy are modified by multiplying the kernals of the various integrals with the factor $S_{ab}$, which is defined as:

$$S_{ab} = \begin{cases} 1 \text{ for non-shielded design} \\ \left(1 - \frac{I_1'(ka)K_1'(kb)}{I_1'(kb)K_1'(ka)}\right) \text{ for shelf-shielded design} \end{cases} \qquad (35)$$

The discretization of the continuous current density can be implemented as follows. First, consider the continuity equation for the current density:

$$\vec{\nabla}\cdot\vec{J}=0 \qquad (36).$$

In analogy with the magnetic field, where a vector potential is introduced, the current density can be expressed as a curl of the function $\vec{s}$, called a "stream function". Specifically:

$$\vec{J} = \vec{\nabla}\times\vec{s} \qquad (37).$$

Because the current density is restricted to flow on the surface of a cylinder of radius $a=\rho_o$ and has only an angular and axial dependence, the relation between the current density and the stream function in cylindrical coordinates is:

$$j_\phi^a(\phi,z)\alpha_\phi + j_z^a(\phi,z)\alpha_z = \frac{\partial S_\rho}{\partial z}\alpha_\phi - \frac{1}{a}\frac{\partial A_\rho}{\partial \phi}\alpha_z, \tag{38}$$

and $S_{92}$ is found from:

$$S_\rho(\phi,z) = -a\int_{-\pi}^{\phi} d\phi' j_z^a(\phi',z). \tag{39}$$

The contour plots of the current density are determined by:

$$S_\rho(x,z) = (n-\tfrac{1}{2})S_{inc} + S_{min} \text{ for } n=1,\ldots,N \tag{40},$$

where N is the number of current contours, $S_{min}$ is the minimum value of the current density, and $S_{inc}$ represents the amount of current between two contour lines. The determination of $S_{inc}$ is:

$$S_{inc} = \frac{S_{max} - S_{min}}{N}, \tag{41}$$

with $S_{max}$ representing the maximum value of the current density. The contours which are generated by this method follow the flow of current and the distance between them corresponds to a current equal to an amount of $S_{inc}$ in Amps. Finally, discrete wires or foil strips are positioned in such a way as to coincide with these contour lines.

For a finite x-gradient Coil with an interstitial gap, a cylinder radius of 21 cm, and a total length of 90 cm, and an interstitial gap of 20–30 cm, the gradient coil assumes the design as shown in FIG. 3. More specifically, constraint points over a 25 cm spherical volume are: a gradient field strength of 40 mT/m linearity along the axis of the gradient of 15% and the third constraint sets the z-component of the current density at the boundaries of the interstitial gap to zero. The set of constraints shown in TABLE 3 is generated.

TABLE 3

| n | $\rho_i$ | $z_i$ | $B_{zSC}(2n)$ |
|---|---|---|---|
| 1 | 0.0010 | 0.000 | 0.000040000 |
| 2 | .125 | 0.0000 | 0.00425 |
| 3 | | $j_{zSC}^n = 0.000000001$ | |

Using these constraints in the aforementioned procedure, the Fourier coefficients are calculated. Hence, the continuous distribution of the current density for the x-gradient coil is obtained. Using the stream function technique, the discrete current distribution of the coil with the interstitial gap is obtained. The discrete version of the current pattern as illustrated in FIG. 3 has 16 positive current loops which each carry about 258.5 Amps for 40 mT/m. The stored energy for this coil configuration is 8.36 Joules at the gradient strength of 40 mT/m. Assuming gradient amplifiers with true current output of 440 Amps. and a true voltage of 600 volts, the estimated rise time is $t_r$=206 μsec. at the gradient strength of 68.1 mT/m. The linearity inside a 25 cm spherical volume is about 15% and the uniformity of the gradient field inside the spherical volume is 20%. TABLE 4 displays a comparison between a conventional whole body self-shielded transverse gradient coil (diameter=68 cm) and the coil of FIG. 3.

TABLE 4

| Property | CONVENTIONAL | INTERSTITIAL |
|---|---|---|
| Strength @ 440 Amps | 27.3 mT/m | 68.1 mT/m |
| SLEW RATE @ 600 Volts | 73 mT/m/msec | 331 mT/m/msec |
| Linearity @ $\rho = \pm 12.5$ cm | 2.5% | 15% |
| Uniformity @ $z = \pm 12.5$ cm | 1.73% | 20% |

Figure 5:
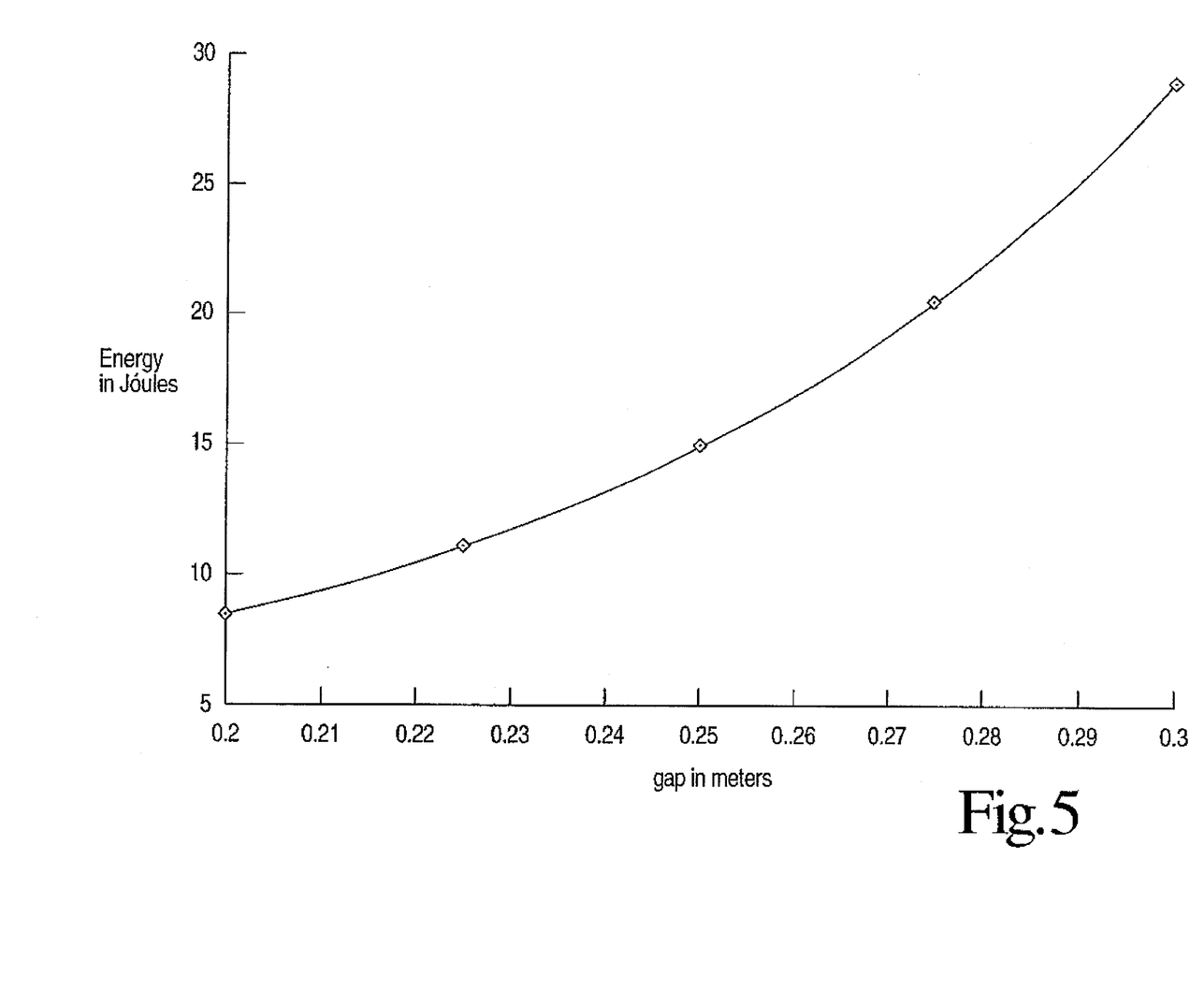
FIG. 5 is a plot of the stored energy versus the interstitial gap of gradient coil assemblies in accordance with the present invention.

It will be appreciated that the gap may be selected to have various widths. As illustrated in FIG. 5, the amount of stored energy varies in accordance with the length of the interstitial gap. It is to be appreciated that the stored energy with a gap of 20 cm is about ⅓ of the energy of a gap of 30 cm.

Various alternate embodiments immediately suggest themselves. For example, the gradient coil assembly may be elliptical rather than cylindrical. As yet another alternative, the gradient coil assembly may be planar or biplanar. Although distributed coils are preferred, the coils may also be bunched in nature. When the radio frequency coil is larger in diameter and placed outside of the gradient coils, a radio frequency shield may be positioned around the exterior of the gradient coil assembly.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A magnetic resonance imaging system comprising:

a single toroidal vacuum dewar containing a superconducting magnet for generating a temporally constant magnetic field axially through a longitudinal bore of the dewar, the vacuum dewar having at least one window adjacent a central portion thereof for providing human access to a central portion of the longitudinal bore;

a patient support which is selectively insertable longitudinally into the bore and movable longitudinally out of the bore;

a gradient coil assembly including a first gradient coil assembly portion fixedly mounted to the patient support and a second gradient coil assembly portion mounted in a fixed, spaced relationship to the first gradient coil assembly portion when the patient support is inserted into the bore, such that a gap is defined centrally within the bore, between the gradient coil assembly portions when the first and second gradient coil portions are in said fixed relationship, whereby human access is provided through the window to a portion of the subject in the gap;

a radio frequency coil mounted adjacent a region of a subject supported on the patient support in the gap between the first and second gradient coil assembly portions;

a radio frequency transmitter connected with the radio frequency coil for selectively transmitting radio frequency magnetic resonance excitation and manipulation signals to the radio frequency coil;

a radio frequency receiver connected with the radio frequency coil for receiving magnetic resonance signals from the region of the patient in the gap;

an image reconstruction processor for reconstructing the received magnetic resonance signals into an image representation;

an image memory for storing the electronic image representation;

a video processor for selectively converting portions of the image representation stored in the image memory into appropriate format for display on a human-readable monitor.

2. A magnetic resonance imaging system comprising:

a toroidal dewar containing a superconducting magnet for generating a temporally constant magnetic field axially through a longitudinal bore of the dewar;

a patient support which is selectively movable longitudinally into and out of the bore;

a gradient coil assembly including a first gradient coil assembly portion and a second gradient coil assembly portion, the gradient coil assembly first and second portions each including a lower section which is fixedly mounted to the patient support and an upper section which is selectively removable to facilitate patient egress and ingress, there being a gap between the gradient coil assembly first and second portions;

a radio frequency coil mounted adjacent a region of a subject supported in the gap between the first and second gradient coil assembly portions;

a radio frequency transmitter connected with the radio frequency coil for selectively transmitting radio frequency magnetic resonance excitation and manipulation signals to the radio frequency coil;

a radio frequency receiver connected with the radio frequency coil for receiving magnetic resonance signals from the region of the patient in the gap;

an image reconstruction processor for reconstructing the received magnetic resonance signals into an image representation;

an image memory for storing the electronic image representation;

a video processor for selectively converting portions of the image representation stored in the image memory into appropriate format for display on a human-readable monitor.

3. The magnetic resonance imaging apparatus as set forth in claim 2, wherein the gradient coil assembly includes distributed winding gradient coils.

4. The magnetic resonance imaging system as set forth in claim 1 wherein the radio frequency coil is disposed in the gap between the first and second gradient coil assembly portions and has open regions therethrough for providing access to a portion of the patient in the gap.

5. A method of magnetic resonance imaging with a magnetic resonance imaging system that includes a toroidal dewar which contains a superconducting magnet assembly that defines an axial bore therein, a patient support which is selectively insertable into and removable from the axial bore, a gradient coil assembly having a first gradient coil assembly portion and a second gradient coil assembly portion which are separated by a patient access gap, the first and second gradient coil assembly portions each having lower sections which are fixedly mounted to the patient support and upper sections which are selectively removable therefrom, and a radio frequency coil assembly having a lower portion which is fixedly supported by the patient support between the first and second gradient coil assembly portions and an upper portion which is selectively positionable between the first and second gradient coil assembly portions, the method comprising:

removing the gradient coil assembly portions upper sections;

positioning a patient on the patient support with the patient's torso below the shoulders in one of the gradient coil assembly lower sections and with the patient's head and neck in the other of the gradient coil assembly lower sections;

connecting the first and second gradient coil assembly upper sections to the first and second gradient assembly lower sections;

disposing the radio frequency coil assembly upper portion over the patient's upper torso portion;

moving the upper torso portion of the patient and the first and second gradient coil assembly portions into the bore;

conducting a magnetic resonance imaging sequence to generate an electronic image representation of at least the upper torso portion of the patient disposed between the first and second gradient coil assembly portions;

selectively displaying at least a portion of the electronic image representation as a human-readable display.

6. A magnetic resonance imaging system comprising:

a toroidal dewar containing a superconducting magnet for generating a temporally constant magnetic field axially through a longitudinal bore of the dewar;

a patient support which is selectively insertable into the bore;

a first cylindrical gradient coil assembly disposed within the longitudinal bore;

a second cylindrical gradient coil assembly disposed within the longitudinal bore spaced from the first cylindrical gradient coil assembly such that a patient access gap is defined therebetween;

a radio frequency coil mounted adjacent a region of a subject supported on the patient support in the patient access gap between the first and second gradient coil assembly portions;

a radio frequency transmitter connected with the radio frequency coil for selectively transmitting radio frequency magnetic resonance excitation and manipulation signals to the radio frequency coil;

a radio frequency receiver connected with the radio frequency coil for receiving magnetic resonance signals from the region of the patient in the patient access gap;

an image reconstruction processor for reconstructing the received magnetic resonance signals into an image representation;

a video processor for selectively converting portions of the image representation stored in the image memory into appropriate format for display on a human-readable monitor.

7. The magnetic resonance imaging system as set forth in claim 6 wherein the toroidal dewar has an open window therein into the bore adjacent the patient access gap between the first and second cylindrical gradient coil assemblies.

\* \* \* \* \*